US012676508B2

(12) United States Patent
Xu

(10) Patent No.: US 12,676,508 B2
(45) Date of Patent: Jul. 7, 2026

(54) ELECTRIC ENERGY TRANSMISSION SYSTEM, AND FLEXIBLE ELECTRIC ENERGY REPEATER, RELAY RESONANCE COIL, IN-VITRO ENERGY CONTROLLER AND IN-VIVO ELECTRIC ENERGY RECEIVER THEREOF

(71) Applicant: Beijing Leading Innovation Medical Valley Co Ltd, Beijing (CN)

(72) Inventor: Tianrui Xu, Beijing (CN)

(73) Assignee: BEIJING LEADING INNOVATION MEDICAL VALLEY CO LTD, Beijing (CN)

( * ) Notice: Subject to any disclaimer, the term of this patent is extended or adjusted under 35 U.S.C. 154(b) by 218 days.

(21) Appl. No.: 18/729,586

(22) PCT Filed: Nov. 14, 2022

(86) PCT No.: PCT/CN2022/131583
§ 371 (c)(1),
(2) Date: Jul. 17, 2024

(87) PCT Pub. No.: WO2023/165163
PCT Pub. Date: Sep. 7, 2023

(65) Prior Publication Data
US 2025/0118994 A1 Apr. 10, 2025

(30) Foreign Application Priority Data

Mar. 2, 2022 (CN) .......................... 202210198870.9

(51) Int. Cl.
*H02J 50/12* (2016.01)
*A61N 1/378* (2006.01)
(Continued)

(52) U.S. Cl.
CPC ............ *H02J 50/12* (2016.02); *A61N 1/3787* (2013.01); *H02J 50/005* (2020.01); *H02J 2105/46* (2026.01)

(58) Field of Classification Search
CPC ...... H02J 50/12; H02J 50/005; H02J 2310/23; A61N 1/3787
See application file for complete search history.

(56) References Cited

U.S. PATENT DOCUMENTS 9,242,103 B2 * 1/2016 Perryman ............ A61N 1/3787
2011/0115430 A1 * 5/2011 Saunamaki ............. H02J 50/12
320/108
(Continued)

FOREIGN PATENT DOCUMENTS

CN 103219807 A 7/2013
CN 103501060 A 1/2014
(Continued)

*Primary Examiner* — Menatoallah Youssef
*Assistant Examiner* — Esayas G Yeshaw
(74) *Attorney, Agent, or Firm* — Polsinelli PC

(57) ABSTRACT

The present invention proposes an electric energy transmission system and a flexible electric energy relay, a relay resonant coil, an extracorporeal energy controller, and an intracorporal electric energy receiver thereof. A flexible electric energy relay is used in conjunction with an extracorporeal energy controller and an intracorporal electric energy receiver to form an electric energy transmission system using coil relay, wherein the flexible electric energy relay includes a relay RF receiving coil and its compensation network circuit, a relay rectification circuit, a VCO circuit, an RF amplification circuit, and an RF emitting antenna, the relay rectification circuit converts low-frequency electromagnetic energy received from the extracorporeal energy controller into direct current, the VCO circuit and the RF amplification circuit are used to amplify and convert the direct current into an RF signal, which is then transmit by the
(Continued)

Relay resonant coil 02

RF emitting antenna to the intracorporal electric energy receiver implanted in a patient's body. The flexible electric energy relay has a flexible structure as a whole, so as to adhere to a surface of skin or clothing. The electric energy transmission system using coil relay of the present invention may also comprise a relay resonant coil.

18 Claims, 5 Drawing Sheets

(51) Int. Cl.
 _H02J 50/00_ (2016.01)
 _H02J 105/46_ (2026.01)

(56) References Cited

U.S. PATENT DOCUMENTS

| | | | | |
|---|---|---|---|---|
| 2014/0252875 | A1 | 9/2014 | Lee | |
| 2014/0375137 | A1* | 12/2014 | Ichikawa | H02J 50/502 |
| | | | | 307/104 |
| 2017/0279315 | A1* | 9/2017 | Sakata | H02M 3/335 |
| 2018/0280708 | A1* | 10/2018 | Escalona | A61N 1/3787 |
| 2022/0077717 | A1* | 3/2022 | Lee | H02J 50/12 |
| 2022/0378303 | A1* | 12/2022 | Melodia | A61M 60/295 |

FOREIGN PATENT DOCUMENTS

| | | |
|---|---|---|
| CN | 103733477 A | 4/2014 |
| CN | 107078559 A | 8/2017 |
| CN | 108233550 A | 6/2018 |
| CN | 114784999 A | 7/2022 |

* cited by examiner

Relay resonant coil 02

Figure 7

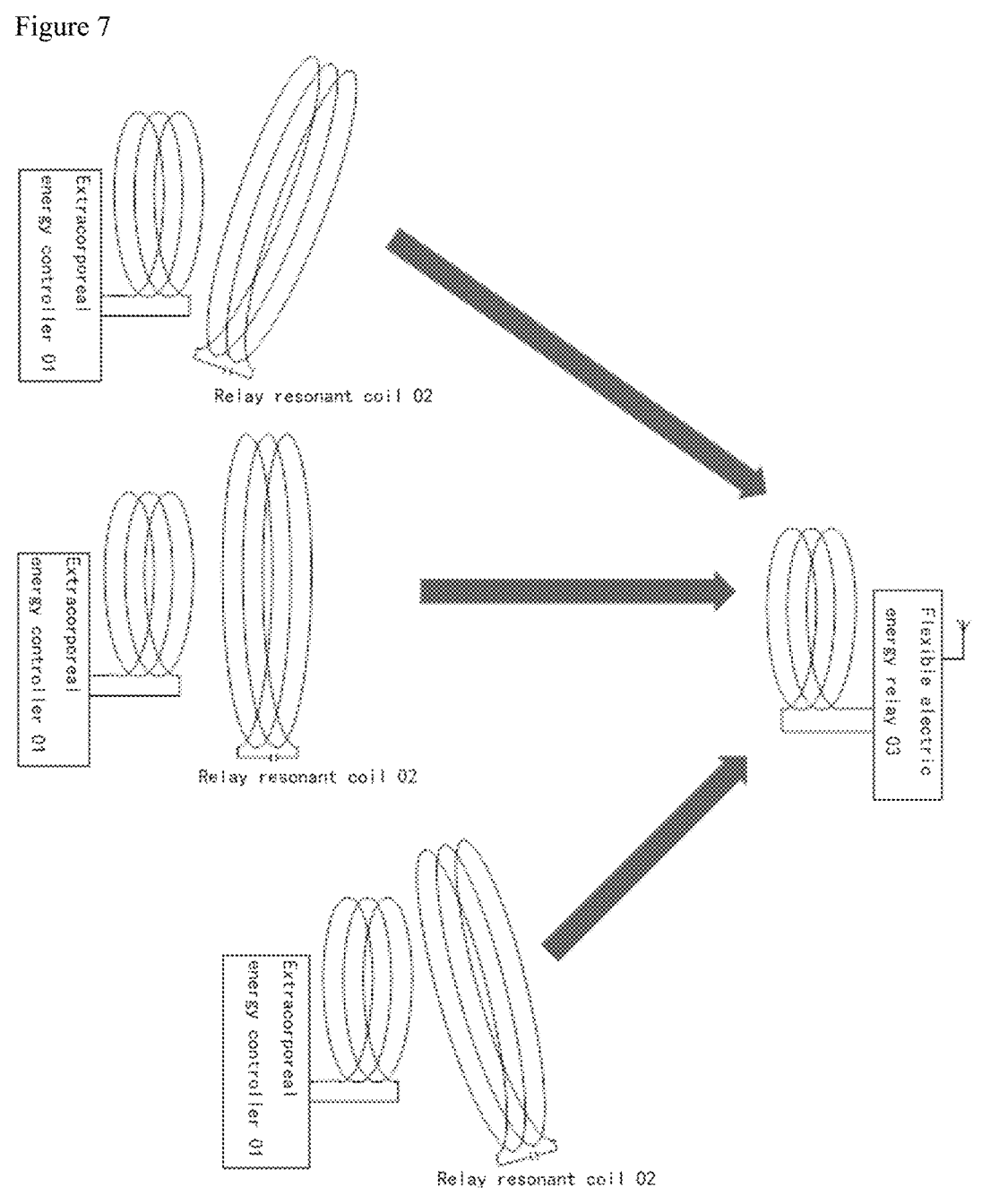

Relay resonant coil 02

Extracorporeal energy controller 01

Relay resonant coil 02

Extracorporeal energy controller 01

Relay resonant coil 02

Extracorporeal energy controller 01

Flexible electric energy relay 03

Figure 8

ELECTRIC ENERGY TRANSMISSION SYSTEM, AND FLEXIBLE ELECTRIC ENERGY REPEATER, RELAY RESONANCE COIL, IN-VITRO ENERGY CONTROLLER AND IN-VIVO ELECTRIC ENERGY RECEIVER THEREOF

TECHNICAL FIELD

The present invention relates to transcutaneous non-contact energy transmission, in particular to an electric energy transmission system using coil relay.

BACKGROUND ART

Unlike implantable battery power supply, the transcutaneous energy transmission system (TETS) is to transmit an extraneous energy source through the human skin to an intracorporal implanted device by way of magnetic fields and electromagnetic induction. That is, an extracorporeal energy controller wirelessly transmits energy to a treatment device implanted in a patient's body through an RF antenna, such as an implantable neural stimulator implanted in the patient's body. Therefore, this type of intracorporal implanted device is not limited by its own carried capacity of electric energy and does not require frequent replacement of batteries; and does not require connection with an extracorporeal energy controller by wire. Therefore, it greatly reduces the patient's pain and also reduces the risk of surgical infection.

In the existing wireless electric energy transmission technologies mentioned above, the entire system consists of two main parts, namely an extracorporeal energy transmitter (extracorporeal energy controller) and an intracorporal implanted energy receiver. The extracorporeal energy controller converts electric energy into high-frequency electromagnetic waves of different frequencies and sends them out. Then, the intracorporal receiver is designed to be able to receive the electromagnetic wave energy of this frequency and convert it into a usable form of electrical energy (direct current or low-frequency).

The transmission distance between the two main parts is limited, resulting in significant limitations on their relative position and direction, which limits the patient's mobility.

And in order to make the intracorporal receiver compatible with nuclear magnetic resonance examination, only inert magnetic designs that are not sensitive to magnetic fields can be used (the inert magnetic designs can use materials of gold, silver platinum iridium alloys, etc.), using high-frequency radio frequency electromagnetic waves as energy carriers, and transmitting electric energy by way of electric field coupling.

The above structure has the following problems: the transmission distance is not far enough (<6 cm), and the transmission power is limited by the battery capacity of the extracorporeal energy controller. Therefore, it limits the patient's range of action.

CN105163800B discloses a wireless implantable power receiver system, wherein a wireless implantable power receiver is disclosed, which can be used in conjunction with various implantable intracorporal devices (including implantable stimulators) and supply power to them. The wireless implantable power receiver is implanted into the patient's body, which cannot solve the problem of insufficient transmission distance of the extracorporeal energy controller mentioned above.

CN208229217U discloses a wearable wireless repeater, program controlled device, and implanted medical system, wherein the wearable wireless repeater needs to be connected to a wire for charging, equipped with a complete control chip and communication module. Therefore, though called a wearable wireless repeater, it is an extracorporeal energy controller in terms of functionality and structure. And due to the need to connect a wire for charging, the mobility range of the patient wearing the wearable wireless repeater is still limited.

The information disclosed in the background section of the present invention is only intended to increase an understanding of the overall background of the present invention, and should not be regarded as acknowledging or implying in any form that the information constitutes the prior art that is already well-known to those skilled in the art.

SUMMARY OF THE INVENTION

A purpose of the present invention is to solve the problem of insufficient energy transmission distance between the extracorporeal energy controller and the implanted device in the patient's body in the implantable treatment system of the prior art, resulting in mobility inconvenience for a patient wearing the implanted device.

To solve the above problem, the present invention inserts a passive electric energy relay between the extracorporeal energy controller and the patient's implanted device. The relay itself does not store electric energy, and its energy comes from the extracorporeal energy controller, and the obtained electric energy is then converted into a high-frequency electromagnetic wave suitable for the patient's implanted device to receive for transmission, replacing the original function of the extracorporeal energy controller in transmitting energy.

Specifically, the present invention provides a flexible electric energy relay used in conjunction with an extracorporeal energy controller and an intracorporal energy receiver to form an electric energy transmission system using coil relay, the flexible electric energy relay comprises a relay RF receiving coil and its compensation network circuit, a relay rectification circuit, a VCO circuit (i.e. voltage controlled oscillator circuit), an RF amplification circuit, and an RF emitting antenna, wherein the relay RF receiving coil is used to receive electromagnetic energy from the extracorporeal energy controller, the compensation network circuit is used for impedance transformation, and the relay RF receiving coil and its compensation network circuit have the same resonant frequency as the extracorporeal energy controller, the relay rectification circuit is used to convert the received electromagnetic energy into direct current, the VCO circuit and the RF amplification circuit are used to amplify and convert the direct current into an RF signal, the RF emitting antenna is used to transmit the RF signal to the intracorporal electric energy receiver implanted in a patient's body, the flexible electric energy relay has a flexible structure as a whole, thereby adhering to a surface of skin or clothing.

Preferably, the electric energy transmission system using coil relay further comprises one or more relay resonant coils which amplify electromagnetic energy emitted by the extracorporeal energy controller, the relay RF receiving coil receives the amplified electromagnetic energy, and the relay RF receiving coil and its compensation network circuit have the same resonant frequency as the extracorporeal energy controller and the relay resonant coil. Further preferably, the relay resonant coil is combined with the relay RF receiving coil to form a planar structure; or the relay resonant coil is combined with an energy controller emitting coil of the extracorporeal energy controller to form a planar structure.

The present invention also provides a relay resonant coil used in conjunction with an extracorporeal energy controller, a flexible electric energy relay, and an intracorporal receiver to form an electric energy transmission system using coil relay, for amplifying and transmitting electromagnetic energy emitted by the extracorporeal energy controller to the flexible electric energy relay having a relay RF receiving coil and its compensation network circuit which have the same resonant frequency as the extracorporeal energy controller and the relay resonant coil, wherein the relay resonant coil is a resonant circuit composed of a relay coil and a resonant circuit in series.

Preferably, the relay resonant coil is combined with the relay RF receiving coil of the flexible electric energy relay to form a planar structure; or the relay resonant coil is combined with an energy controller emitting coil of the extracorporeal energy controller to form a planar structure.

The present invention also provides an extracorporeal energy controller used in conjunction with a flexible electric energy relay and an intracorporal electric energy receiver to form an electric energy transmission system using coil relay, wherein the extracorporeal energy controller transmits energy wirelessly to the flexible electric energy relay by way of electromagnetic coupling resonance, and the extracorporeal energy controller and the flexible electric energy relay have the same resonant frequency, the extracorporeal energy controller comprises a power supply system, a main control chip, a high-frequency inverter circuit, a compensation network, an energy controller emitting coil, a communication module, a storage module, and a measurement circuit, the power supply system is used to power the extracorporeal energy controller, the storage module is used to store system setting parameters and operational data, the measurement circuit measures operational parameters of the high-frequency inverter circuit, the main control chip controls operation of the extracorporeal energy controller, wherein the main control chip controls the high-frequency inverter circuit and adjusts and controls resonant frequency and switching frequency based on the operational parameters feedback from the measurement circuit, the energy controller emitting coil is used to wirelessly transmit electric energy to the flexible electric energy relay at a resonant frequency.

In the above extracorporeal energy controller of the present invention, preferably the storage module further stores a control function, by using which the main control chip calculates relevant parameters required to adjust and control resonant frequency and switching frequency based on the operational parameters feedback from the measurement circuit. Or preferably, the storage module further stores a parameter mapping table, by inquiring which the main control chip determines relevant parameters required to adjust and control resonant frequency and switching frequency based on the operational parameters feedback from the measurement circuit.

In the above extracorporeal energy controller of the present invention, preferably the extracorporeal energy controller is capable of communicating with other devices including an electronic device installed with upper computer software through the communication module.

The present invention also provides an intracorporal electric energy receiver for implantation into a patient's body, and in conjunction with an extracorporeal energy controller and a flexible electric energy relay to form an electric energy transmission system using coil relay, and wirelessly receiving electric energy from the flexible electric energy relay which communicates with the extracorporeal energy controller and receives electric energy from the extracorporeal energy controller, the intracorporal electric energy receiver is configured to include an intracorporal RF receiving antenna, an intracorporal impedance matching circuit, an intracorporal rectification circuit, and an intracorporal energy storage circuit, the intracorporal RF receiving antenna is used to receive electromagnetic energy transmit from the RF emitting antenna of the flexible electric energy relay, the intracorporal impedance matching circuit is used to achieve impedance transformation to match impedance of the RF emitting antenna, the intracorporal rectification circuit is used to rectify the received electromagnetic energy into direct current energy, and the intracorporal energy storage circuit is used to store the direct current energy.

In the above intracorporal electric energy receiver, the intracorporal energy storage circuit is a capacitive energy storage system.

The present invention also provides an electric energy transmission system using coil relay, comprising an extracorporeal energy controller, one or more flexible electric energy relays, and one or more intracorporal electric energy receivers, wherein the extracorporeal energy controller and the flexible electric energy relay have the same resonant frequency, and electric energy is wirelessly transmitted from the extracorporeal energy controller to the flexible electric energy relay by way of electromagnetic coupling resonance; the flexible electric energy relay converts the received electromagnetic energy into direct current which is then converted into an RF signal transmit to the intracorporal electric energy receiver.

In the above electric energy transmission system using coil relay, the flexible electric energy relay may include a VCO circuit and an RF amplification circuit, for converting the direct current into an RF signal.

In the above electric energy transmission system using coil relay, it may also comprise one or more relay resonant coils, wherein the extracorporeal energy controller, the relay resonant coil and the flexible electric energy relay have the same resonant frequency, and electric energy is transmitted from the extracorporeal energy controller, through resonant amplified by the relay resonant coil, to the flexible electric energy relay by way of electromagnetic coupling resonance.

Through the above structure, the coupling relationship between the original extracorporeal energy controller and the patient's implanted device can be reduced, and the electric energy transmission distance between the extracorporeal energy controller and the patient wearing a flexible energy relay can be increased. The flexible electric energy relay replaces the original extracorporeal energy controllers to complete the functions of electric energy conversion and transmission. The electric energy relay itself does not have a battery, which receives electric energy transmitted by the extracorporeal energy controller and converts it into a form of electric energy required for the patient's implanted device.

The electric energy relay adopts a flexible design, which can fit the human skin better. Due to the fact that the electric energy relay itself does not have various complex components and batteries required for an extracorporeal energy controller, it can be designed to be more comfortable and suitable for wearing.

Therefore, the extracorporeal energy controller can transport energy to a relay in various forms, such as electromagnetic coupling coils, capacitive coupling, ultrasonic energy transmission, laser energy transmission, etc.

The methods and devices of the present invention have other performances and advantages that will be apparent from the accompanying drawings and subsequent specific embodiments incorporated herein, or will be described in detail in the accompanying drawings and subsequent specific embodiments, which together serve to explain the specific principles of the present invention.

BRIEF DESCRIPTION OF DRAWINGS

FIG. 7 shows a schematic diagram of an embodiment that utilizes a plurality of extracorporeal energy controllers to simultaneously transmit electric energy to a flexible electric energy relay through a plurality of relay resonant coils in different directions.

FIG. 8 shows a schematic diagram of another embodiment that utilizes a plurality of extracorporeal energy controllers to simultaneously transmit electric energy to a flexible electric energy relay through a plurality of relay resonant coils in different directions.

DETAILED DESCRIPTION OF EMBODIMENTS

Now, specific reference will be made to the various embodiments of the present invention, and examples of these embodiments are shown in the accompanying drawings and the following description. Although the present invention is described in conjunction with exemplary embodiments, it should be understood that this description is not intended to limit the present invention to those exemplary embodiments. On the contrary, the present invention aims to cover not only these exemplary embodiments, but also various substitutions, modifications, equivalents, and other embodiments that can be included within the spirit and scope of the present invention as defined by the claims.

Herein, exemplary embodiments of the present invention will be described in detail with reference to the accompanying drawings. These exemplary embodiments are examples and can be implemented in various forms by those skilled in the art. Therefore, the present invention is not limited to the exemplary embodiments described herein.

The electric energy transmission system using coil relay of the present invention is a transcutaneous non-contact energy transmission system.

Figure 1:
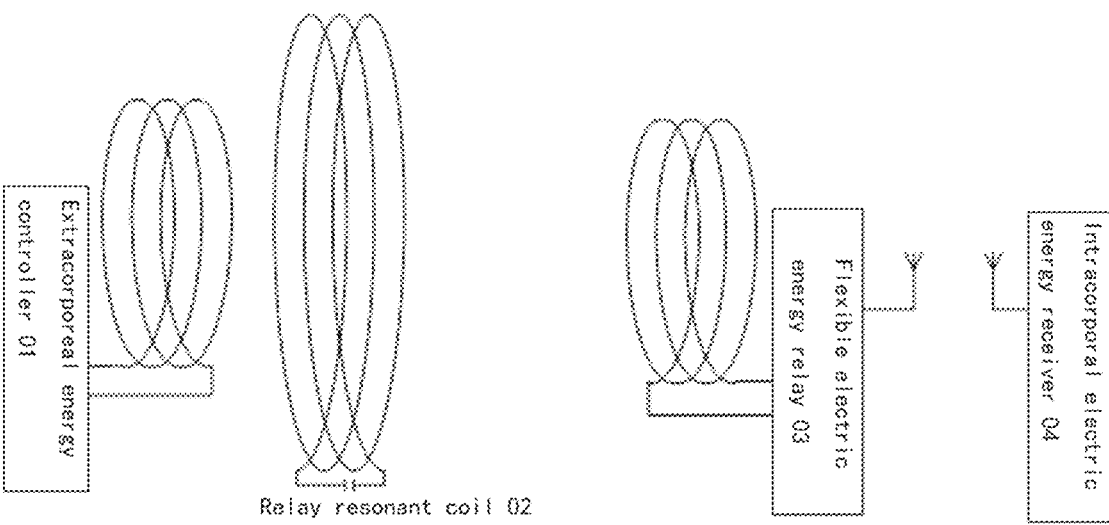
FIG. 1 shows an electric energy transmission system using coil relay of the present invention.

As shown in FIG. 1, the electric energy transmission system using coil relay of the present invention comprises an extracorporeal energy controller 01, one or more relay resonant coils 02, one or more flexible electric energy relays 03, and one or more intracorporal receivers 04.

The resonant frequencies of the coil of the extracorporeal energy controller 01, the relay resonant coil 02, and the coil of the flexible electric energy relay 03 are set to the same frequency. Electric energy is transmitted from the extracorporeal energy controller 01, through resonant amplified by the relay resonant coil 02, to a receiving coil of the flexible electric energy relay 03 by way of electromagnetic coupling resonance.

Flexible Electric Energy Relay

Figure 2:
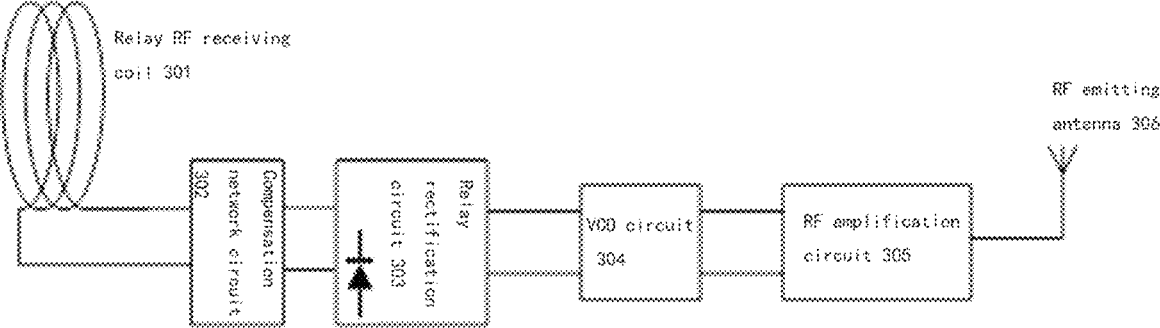
FIG. 2 shows a functional block diagram of a flexible electric energy relay of the present invention.

As shown in FIG. 2, it illustrates a functional block diagram of a flexible electric energy relay of the present invention.

The flexible electric energy relay 03 of the present invention is used in conjunction with an extracorporeal energy controller 01 and an intracorporal receiver 04 to form an electric energy transmission system using coil relay.

The flexible electric energy relay 03 comprises a relay RF receiving coil 301 and its compensation network circuit 302, a relay rectification circuit 303, a VCO circuit 304, an RF amplification circuit 305, and an RF emitting antenna 306.

The relay RF receiving coil 301 is used to receive electromagnetic energy from the extracorporeal energy controller 01. The compensation network circuit 302 is used for impedance transformation to change the impedance characteristics of the flexible electric energy relay 03 and improve its ability to receive radio energy. Wherein the relay RF receiving coil 301 and its compensation network circuit 302 have the same resonant frequency as the extracorporeal energy controller 01. The relay rectification circuit 303 is used to convert the received electromagnetic energy with a relatively low frequency into direct current. The VCO circuit 304 and the RF amplification circuit 305 are used to amplify and convert the direct current into an RF signal with a relatively high frequency. The RF emitting antenna 306 is used to transmit the RF signal to the intracorporal receiver 04 implanted in a patient's body.

The flexible electric energy relay 03 has a flexible structure as a whole, thereby adhering to a surface of skin or clothing.

In the electric energy transmission system using coil relay mentioned above, it may also include a relay resonant coil 02. At this point, the relay resonant coil 02 amplifies the electromagnetic energy emitted by the extracorporeal energy controller 01. The relay RF receiving coil 301 of the flexible electric energy relay 03 receives amplified electromagnetic energy from the relay resonant coil 02. In this case, the relay RF receiving coil 301 and its compensation network circuit 302 have the same resonant frequency as the extracorporeal energy controller 01 and the relay resonant coil 02.

Figure 4:
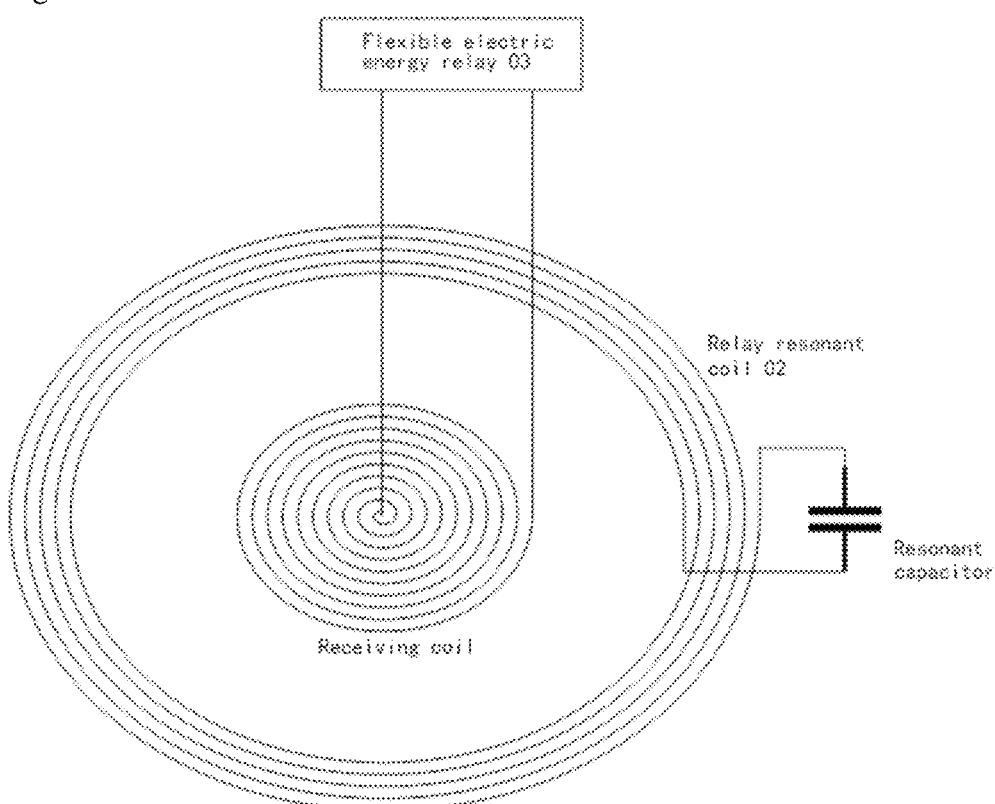
FIG. 4 shows a schematic diagram of combination of a relay RF receiving coil of a flexible electric energy relay and a relay coil of a relay resonant coil in the present invention.
Figure 5:
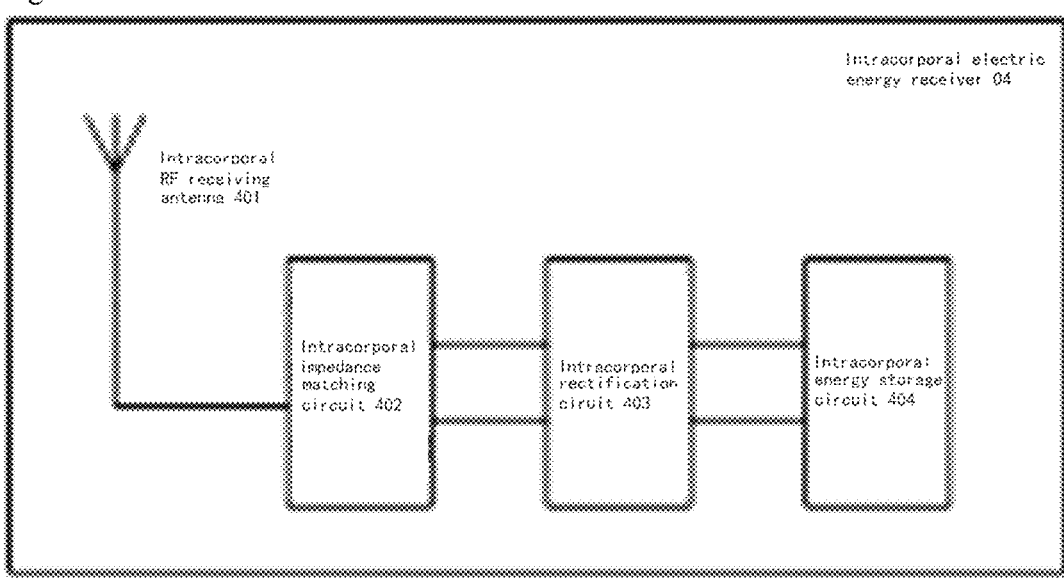
FIG. 5 shows a functional block diagram of an intracorporal electric energy receiver of the present invention.

As shown in FIG. 4, in the electric energy transmission system using coil relay comprising the relay resonant coil 02 mentioned above, the relay resonant coil 02 and the relay RF receiving coil 301 may be combined together to form a planar structure.

Figure 3:
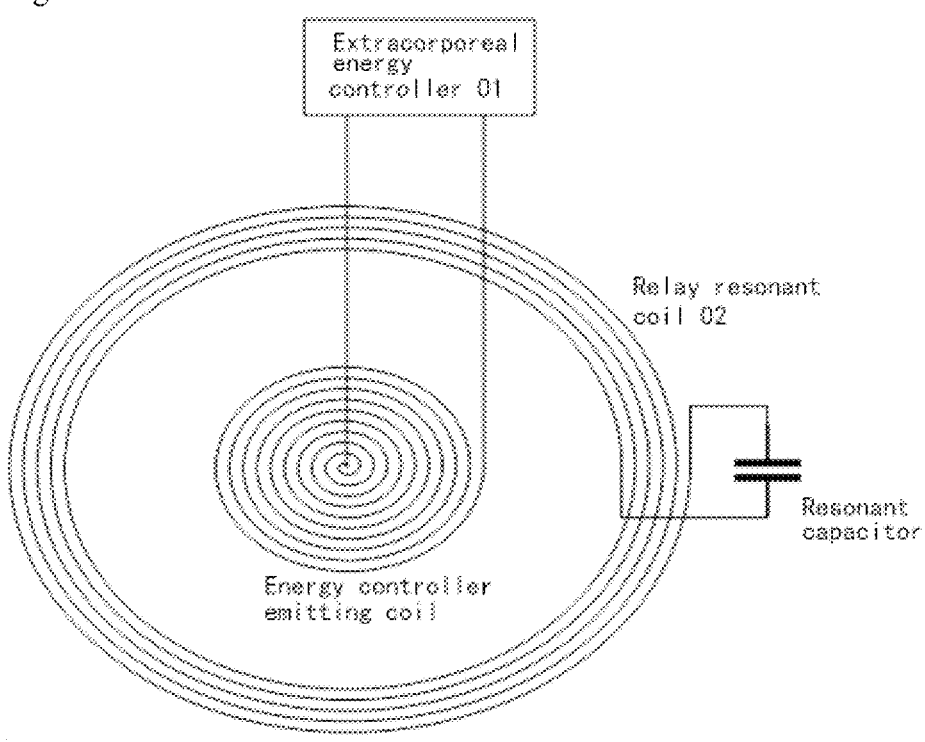
FIG. 3 shows a schematic diagram of combination of a relay coil of a relay resonant coil and an energy controller emitting coil of an extracorporeal energy controller in the present invention.

As shown in FIG. 3, in the electric energy transmission system using coil relay comprising the relay resonant coil 02 mentioned above, the relay resonant coil 02 and the energy controller emitting coil 105 of the extracorporeal energy controller 01 may be combined together to form a planar structure.

Intracorporal Electric Energy Receiver

The intracorporal electric energy receiver 04 is for implantation into a patient's body, and forms an electric energy transmission system using coil relay in conjunction with the extracorporeal energy controller 01 and the flexible electric energy relay 03, and wirelessly receives electric energy from the flexible electric energy relay 03. The flexible electric energy relay 03 communicates with the extracorporeal energy controller 01 and receives electric energy from the extracorporeal energy controller 01.

The intracorporal electric energy receiver 04 comprises an intracorporal RF receiving antenna 401, an intracorporal impedance matching circuit 402, an intracorporal rectification circuit 403, and an intracorporal energy storage circuit 404.

The intracorporal RF receiving antenna 401 is used to receive electromagnetic energy transmitted from the RF emitting antenna 306 of the flexible electric energy relay 03. The intracorporal impedance matching circuit 402 is used to achieve impedance transformation to match impedance of the RF emitting antenna 306. The intracorporal rectification circuit 403 is used to rectify the received electromagnetic energy into direct current energy, which can be used by an intracorporal implanted device or stored in the intracorporal energy storage circuit 404. The intracorporal energy storage circuit 404 is used to store the direct current energy.

The above intracorporal energy storage circuit 404 can be a capacitive energy storage system.

Extracorporeal Energy Controller 01

As mentioned above, the extracorporeal energy controller 01 of the present invention is used in conjunction with a flexible electric energy relay 03 and an intracorporal electric energy receiver 04 to form an electric energy transmission system using coil relay, wherein the extracorporeal energy controller 01 transmits electric energy wirelessly to the flexible electric energy relay 03 by way of electromagnetic coupling resonance, and the extracorporeal energy controller 01 and the flexible electric energy relay 03 have the same resonant frequency.

Figure 6:
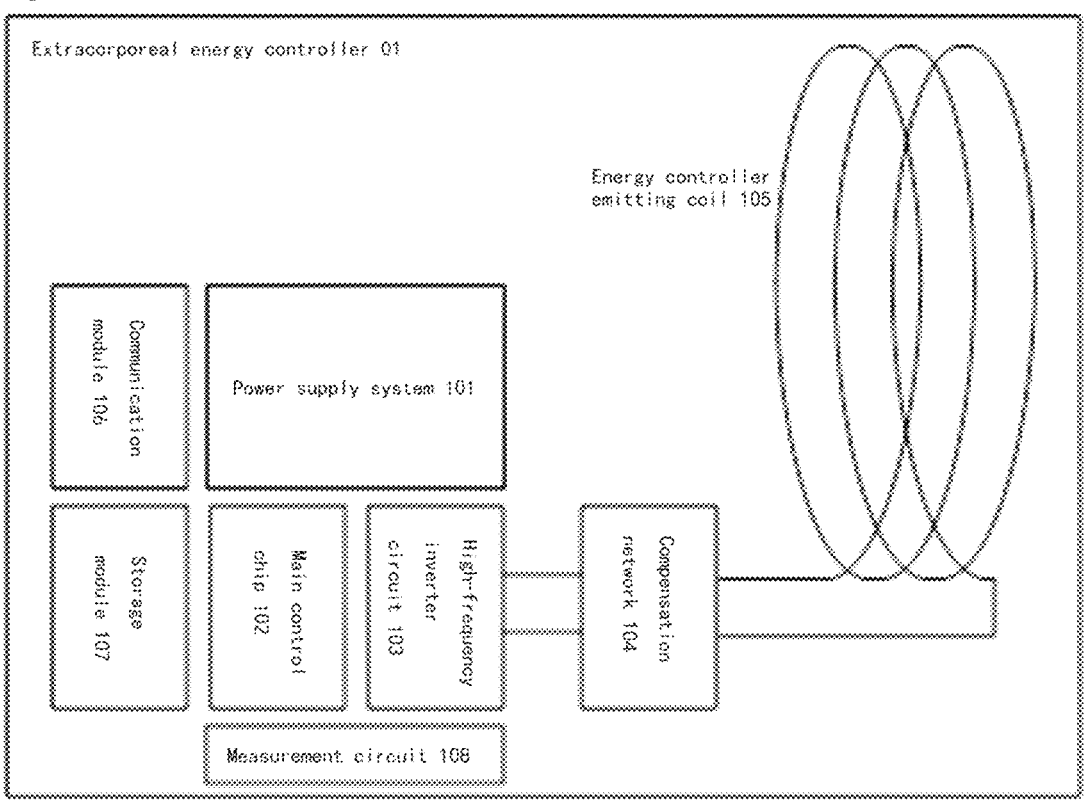
FIG. 6 shows a functional block diagram of an extracorporeal energy controller of the present invention.

FIG. 6 shows a functional block diagram of an extracorporeal energy controller of the present invention.

As shown in FIG. 6, the extracorporeal energy controller 01 is configured to comprise a power supply system 101, a main control chip 102, a high-frequency inverter circuit 103, a compensation network 104, an energy controller emitting coil 105, a communication module 106, a storage module 107, and a measurement circuit 108.

The extracorporeal energy controller 01 can exchange information with other systems through the communication module 106, and can also receive information from an upper computer software which can be software installed on tablets, laptops, or PCs, and can exchange information with the extracorporeal energy controller 01 through a Bluetooth module.

The storage module 107 can store relevant parameters of the system configuration and relevant data recorded during system operation. These data will not be lost even the system is powered off, and can be read by the main control chip after the system is powered on again.

The main control chip 102 is the control core of the extracorporeal energy controller 01, in addition to communicating with the upper computer, which also needs to control the high-frequency inverter circuit 103.

This system uses magnetic coupling resonance to achieve wireless electric energy transmission between the extracorporeal energy controller 01 and the flexible electric energy relay 03. This way needs to control the resonant frequency according to external conditions during operation, in order to achieve the goal of maximum wireless electric energy transmission power or maximum receiving voltage at the receiving end. The optimization function varies for different control objectives, and the control algorithm also varies.

The measurement circuit 108 measures operational parameters of the high-frequency inverter circuit, and feedbacks the measurement result to the main control chip. The main control chip adjusts the switching frequency based on the measurement feedback. According to the complexity of the control algorithm, the control way can be divided into function calculation method and mapping table method. The function calculation method is a control method that performs a series of calculations based on the feedback data to obtain the final control parameters. The mapping table method is to calculate all possible inputs of the control algorithm, store the results as a data table, and obtain control parameters through querying the table in actual operation.

The extracorporeal controller 01 can determine its own control objectives and select corresponding control algorithms based on the working status of the intracorporal implantable medical device, and store relevant information in the storage module 107, and when conditions are met, which can be uploaded to the upper computer.

Relay Resonant Coil

The relay resonant coil 02 of the present invention is used in conjunction with an extracorporeal energy controller 01, a flexible electric energy relay 03, and an intracorporal receiver 04 to form an electric energy transmission system using coil relay.

As shown in FIGS. 3 and 4, the relay resonant coil 02 of the present invention is a resonant circuit composed of a relay coil 201 and a resonant circuit 202 in series. The relay resonant coil 02 can be in the form of a printed circuit or in the form of copper wire winding.

As shown in FIG. 4, the relay resonant coil 02 of the present invention can be combined with the relay RF receiving coil 301 of the flexible electric energy relay 03 to form a planar structure.

Different from the scheme of FIG. 4, FIG. 3 shows that the relay resonant coil 02 is combined with an energy controller emitting coil 105 of the extracorporeal energy controller 01 to form a planar structure.

In specific implementation, the relay resonant coil 02 is not necessarily required. If the transmission distance is close, just the extracorporeal energy controller 01 can be used to directly transmit electric energy to the flexible electric energy relay 03.

The relay resonant coil 02 has the following functions:

Function 1: Amplify the intensity of electromagnetic waves through electromagnetic resonance, thereby increasing transmission distance and power;

Function 2: Adjust the transmission direction of electromagnetic waves through one or more relay resonant coils 02;

Function 3: A plurality of extracorporeal energy controllers 01, through adjustment of a plurality of relay resonant coils 02, play a role of electromagnetic focusing, allowing the plurality of extracorporeal energy controllers to simultaneously transmit electric energy to a flexible electric energy relay in different directions, thereby enabling the flexible electric energy relay 03 to obtain more or more stable electric energy, as shown in FIG. 7.

① In function 1 and function 2, the relay resonant coil 02 can be placed independently, as shown in FIG. 1;

② It can also be made together with the coil of the extracorporeal energy controller, so that it is in a same plane as the energy controller emitting coil 105 of the extracorporeal energy controller 01 and placed in a concentric circle, as shown in FIG. 3;

③ It can also be made together with the relay RF receiving coil 301 of the flexible electric energy relay 03, so that it is in a same plane as the relay RF receiving coil 301 and placed in a concentric circle, as shown in FIG. 4;

The above three ways can be used independently, or two or three can be used together.

Figure 8:
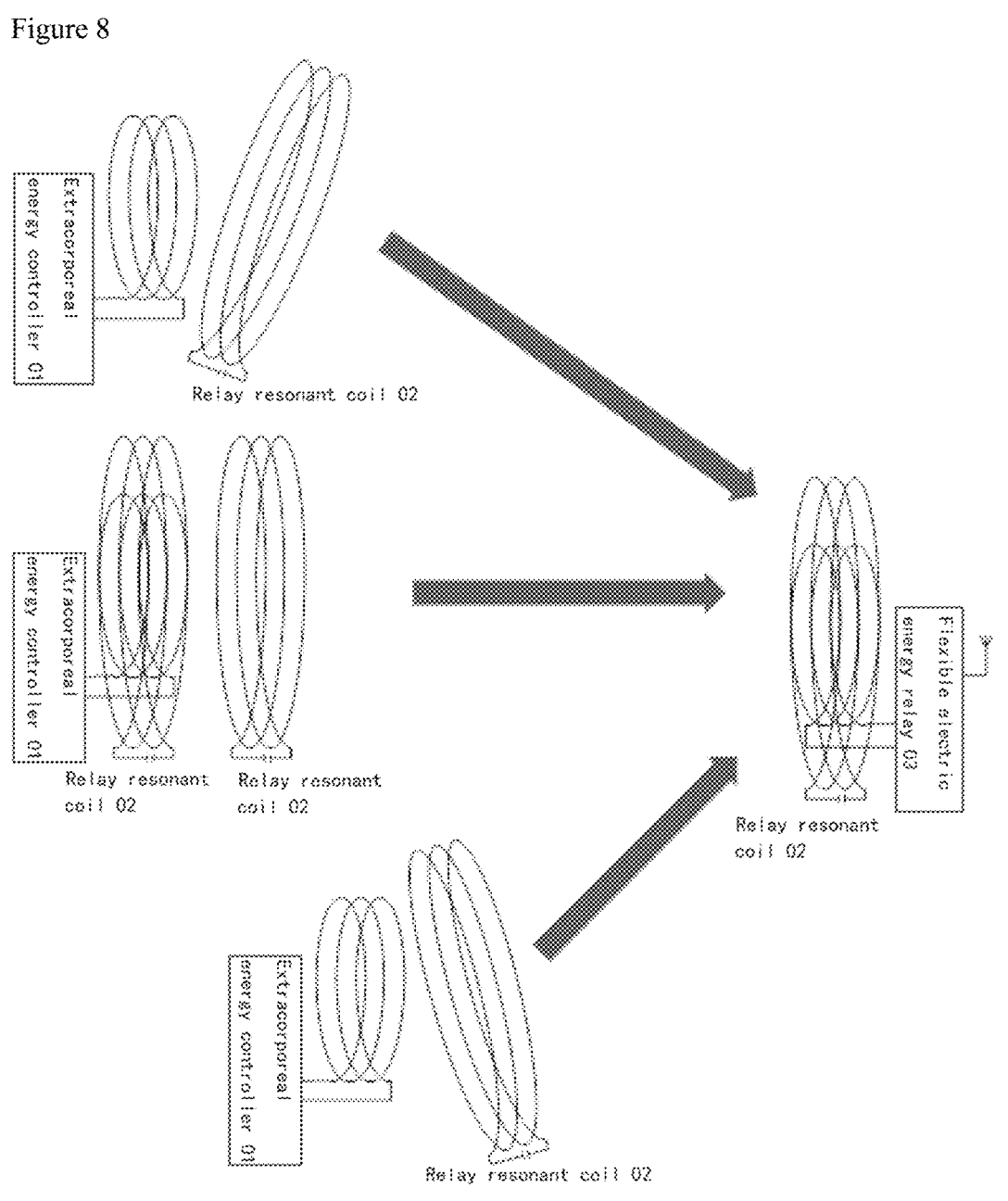

In addition, for the use of the relay resonant coil 02 in function 3, the implementation examples in ①, ②, and ③ can also be referred to for combined use, as shown in FIG. 8.

The aforementioned description of the specific exemplary embodiments of the present invention is for the purpose of illustration and exemplification. These descriptions are not intended to exhaust the present invention or limit it to the precise form disclosed, and it is evident that many changes and variations can be made based on the above teachings. The purpose of selecting and describing exemplary embodiments is to explain the specific principles and practical applications of the present invention, so that other technical personnel in the art can implement and utilize various exemplary embodiments of the present invention, as well as various choices and changes. The scope of the present invention is intended to be limited by the accompanying claims and their equivalent forms.

The invention claimed is:

1. A flexible electric energy relay (03) used in conjunction with an extracorporeal energy controller (01) and an intracorporal electric energy receiver (04) to form an electric energy transmission system using coil relay, the flexible electric energy relay (03) comprising a relay RF receiving coil (301) and its compensation network circuit (302), a relay rectification circuit (303), a VCO circuit (304), an RF amplification circuit (305), and an RF emitting antenna (306), wherein the relay RF receiving coil (301) is used to receive electromagnetic energy from the extracorporeal energy controller (01), the compensation network circuit (302) is used for impedance transformation, and the relay RF receiving coil (301) and its compensation network circuit (302) are configured with the same resonant frequency as the extracorporeal energy controller (01), the relay rectification circuit (303) is used to convert the received electromagnetic energy into direct current, the VCO circuit (304) and the RF amplification circuit (305) are used to amplify and convert the direct current into an RF signal, the RF emitting antenna (306) is used to transmit the RF signal to the intracorporal electric energy receiver (04) implanted in a patient's body, the flexible electric energy relay (03) has a flexible structure as a whole, thereby adhering to a surface of skin or clothing.

2. The flexible electric energy relay (03) according to claim 1, wherein the electric energy transmission system using coil relay further comprises one or more relay resonant coils (02) which amplify electromagnetic energy emitted by the extracorporeal energy controller (01), the relay RF receiving coil (301) receives the amplified electromagnetic energy, and the relay RF receiving coil (301) and its compensation network circuit (302) are configured with the same resonant frequency as the extracorporeal energy controller (01) and the relay resonant coil (02).

3. The flexible electric energy relay (03) according to claim 2, wherein the relay resonant coil (02) is combined with the relay RF receiving coil (301) to form a planar structure.

4. The flexible electric energy relay (03) according to claim 2, wherein the relay resonant coil (02) is combined with an energy controller emitting coil (105) of the extracorporeal energy controller (01) to form a planar structure.

5. A relay resonant coil (02) used in conjunction with an extracorporeal energy controller (01), a flexible electric energy relay (03), and an intracorporal receiver (04) to form an electric energy transmission system using coil relay, for amplifying and transmitting electromagnetic energy emitted by the extracorporeal energy controller (01) to the flexible electric energy relay (03) having a relay RF receiving coil (301) and its compensation network circuit (302) which are configured with the same resonant frequency as the extracorporeal energy controller (01) and the relay resonant coil (02), wherein the relay resonant coil (02) is a resonant circuit composed of a relay coil (201) and a resonant circuit (202) in series.

6. The relay resonant coil (02) according to claim 5, wherein the relay resonant coil (02) is combined with the relay RF receiving coil (301) of the flexible electric energy relay (03) to form a planar structure.

7. The relay resonant coil (02) according to claim 5, wherein the relay resonant coil (02) is combined with an energy controller emitting coil (105) of the extracorporeal energy controller (01) to form a planar structure.

8. An extracorporeal energy controller (01) used in conjunction with a flexible electric energy relay (03) and an intracorporal electric energy receiver (04) to form an electric energy transmission system using coil relay, wherein the extracorporeal energy controller (01) transmits electric energy wirelessly to the flexible electric energy relay (03) by way of electromagnetic coupling resonance, and the extracorporeal energy controller (01) and the flexible electric energy relay (03) are configured with the same resonant frequency, the extracorporeal energy controller (01) comprises a power supply system (101), a main control chip (102), a high-frequency inverter circuit (103), a compensation network (104), an energy controller emitting coil (105), a communication module (106), a storage module (107), and a measurement circuit (108), the power supply system (101) is used to power the extracorporeal energy controller (01), the storage module (107) is used to store system setting parameters and operational data, the measurement circuit (108) measures operational parameters of the high-frequency inverter circuit (103), the main control chip (102) controls operation of the extracorporeal energy controller (01), wherein the main control chip (102) controls the high-frequency inverter circuit (103) and adjusts and controls resonant frequency and switching frequency based on the operational parameters feedback from the measurement circuit (108), the energy controller emitting coil (105) is used to wirelessly transmit electric energy to the flexible electric energy relay (03) at a resonant frequency.

9. The extracorporeal energy controller (01) according to claim 8, wherein the storage module (107) further stores a control function, by using which the main control chip (102) calculates relevant parameters required to adjust and control resonant frequency and switching frequency based on the operational parameters fedback from the measurement circuit (108).

10. The extracorporeal energy controller (01) according to claim 8, wherein the storage module (107) further stores a parameter mapping table, by inquiring which the main control chip (102) determines relevant parameters required to adjust and control resonant frequency and switching frequency based on the operational parameters fedback from the measurement circuit (108).

11. The extracorporeal energy controller (01) according to claim 8, wherein the extracorporeal energy controller (01) is capable of communicating with other devices including an electronic device installed with upper computer software through the communication module (106).

12. The extracorporeal energy controller (01) according to claim 8, wherein the electric energy transmission system using coil relay further comprises a relay resonant coil (02) which amplifies electromagnetic energy emitted by the extracorporeal energy controller (01), and the flexible electric energy relay (03) receives the amplified electromagnetic energy, wherein the extracorporeal energy controller (01) has the same resonant frequency as the relay resonant coil (02) and the flexible electric energy relay (03).

13. An intracorporal electric energy receiver (04), for implantation into a patient's body, and in conjunction with an extracorporeal energy controller (01) and a flexible electric energy relay (03) to form an electric energy transmission system using coil relay, and wirelessly receiving electric energy from the flexible electric energy relay (03) which communicates with the extracorporeal energy controller (01) and receives electric energy from the extracorporeal energy controller (01), the intracorporal electric energy receiver (04) is configured to include an intracorporal RF receiving antenna (401), an intracorporal impedance matching circuit (402), an intracorporal rectification circuit (403), and an intracorporal energy storage circuit (404), the intracorporal RF receiving antenna (401) is used to receive electromagnetic energy transmitted from the RF emitting antenna (306) of the flexible electric energy relay (03), the intracorporal impedance matching circuit (402) is used to achieve impedance transformation to match impedance of the RF emitting antenna (306), the intracorporal rectification circuit (403) is used to rectify the received electromagnetic energy into direct current energy, and the intracorporal energy storage circuit (404) is used to store the direct current energy.

14. The intracorporal electric energy receiver (04) according to claim 13, wherein the intracorporal energy storage circuit (404) is a capacitive energy storage system.

15. The intracorporal electric energy receiver (04) according to claim 13, wherein the electric energy transmission system using coil relay further comprises one or more relay resonant coils (02), the flexible electric energy relay (03) has the same resonant frequency as the extracorporeal energy controller (01) and the relay resonant coil (02), the relay resonant coil (02) makes resonant amplification to electromagnetic energy emitted by the extracorporeal energy controller (01), and the flexible electric energy relay (03) receives the amplified electromagnetic energy.

16. An electric energy transmission system using coil relay, comprising an extracorporeal energy controller (01), one or more flexible electric energy relays (03), and one or more intracorporal electric energy receivers (04), wherein the extracorporeal energy controller (01) and the flexible electric energy relay (03) are configured with the same resonant frequency, and electric energy is wirelessly transmitted from the extracorporeal energy controller (01) to the flexible electric energy relay (03) by way of electromagnetic coupling resonance; the flexible electric energy relay (03) converts the received electromagnetic energy into direct current which is then converted into an RF signal to transmit to the intracorporal electric energy receiver (04).

17. The electric energy transmission system using coil relay according to claim 16, wherein the flexible electric energy relay (03) includes a VCO circuit (304) and an RF amplification circuit (305), for converting the direct current into an RF signal.

18. The electric energy transmission system using coil relay according to claim 16, further comprising one or more relay resonant coils (02), wherein the extracorporeal energy controller (01), the relay resonant coil (02) and the flexible electric energy relay (03) have the same resonant frequency, and electric energy is transmitted from the extracorporeal energy controller (01), through resonant amplified by the relay resonant coil (02), to the flexible electric energy relay (03) by way of electromagnetic coupling resonance.

* * * * *